(12) United States Patent
Davis

(10) Patent No.: US 9,725,328 B1
(45) Date of Patent: Aug. 8, 2017

(54) MOLECULAR SIEVE SSZ-104, ITS SYNTHESIS AND USE

(71) Applicant: Chevron U.S.A. Inc., San Ramon, CA (US)

(72) Inventor: Tracy Margaret Davis, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/160,466

(22) Filed: May 20, 2016

(51) Int. Cl.
| | |
|---|---|
| *C01B 39/48* | (2006.01) |
| *B01J 29/70* | (2006.01) |
| *C07C 1/20* | (2006.01) |
| *B01J 29/76* | (2006.01) |
| *B01J 37/04* | (2006.01) |
| *B01J 37/00* | (2006.01) |
| *B01D 53/94* | (2006.01) |

(52) U.S. Cl.
CPC .......... *C01B 39/48* (2013.01); *B01D 53/9418* (2013.01); *B01J 29/70* (2013.01); *B01J 29/76* (2013.01); *B01J 37/0018* (2013.01); *B01J 37/04* (2013.01); *C07C 1/20* (2013.01); *B01D 2255/50* (2013.01); *C07C 2529/70* (2013.01)

(58) Field of Classification Search
CPC .......... C01B 39/48; B01J 29/70; B01J 29/76; B01D 53/9418; C07C 1/20; C07C 2529/70
See application file for complete search history.

(56) References Cited

U.S. PATENT DOCUMENTS

| | | | | |
|---|---|---|---|---|
| 9,216,911 | B2 * | 12/2015 | Elomari | ................ C01B 39/48 |
| 2002/0081262 | A1 * | 6/2002 | Elomari | ................ B01D 53/86 |
| | | | | 423/704 |
| 2004/0191167 | A1 * | 9/2004 | Elomari | ................ C01B 39/026 |
| | | | | 423/706 |
| 2005/0042169 | A1 * | 2/2005 | Elomari | ................ C01B 37/005 |
| | | | | 423/706 |
| 2016/0068401 | A1 * | 3/2016 | Davis | ................ C01B 39/48 |
| | | | | 423/704 |

FOREIGN PATENT DOCUMENTS

| | | |
|---|---|---|
| GB | 925017 | 5/1963 |
| GB | CA 2913061 A1 * 11/2013 | ................ C10L 1/06 |

* cited by examiner

*Primary Examiner* — David M Brunsman
(74) *Attorney, Agent, or Firm* — Terrence M. Flaherty

(57) ABSTRACT

Disclosed herein is a new crystalline molecular sieve designated SSZ-104, its synthesis in the presence of a structure directing agent comprising N-cyclohexylmethyl-N-ethylpyrrolidinium cations, and its use as an adsorbent and a catalyst.

15 Claims, 2 Drawing Sheets

MOLECULAR SIEVE SSZ-104, ITS SYNTHESIS AND USE

TECHNICAL FIELD

This disclosure relates to a new crystalline molecular sieve designated SSZ-104, its synthesis, and its use as an adsorbent and as a catalyst.

BACKGROUND

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

According to the present disclosure, a new molecular sieve structure, designated SSZ-104, and having a unique X-ray diffraction pattern has now been synthesized using N-cyclohexylmethyl-N-ethylpyrrolidinium cations as a structure directing agent.

SUMMARY

The present disclosure is directed to a new family of crystalline molecular sieves with unique properties, designated herein as "molecular sieve SSZ-104" or simply "SSZ-104."

In one aspect, there is provided a crystalline molecular sieve having, in its calcined form, an X-ray diffraction pattern including at least the peaks set forth in Table 2 below.

The molecular sieve has, in its calcined form, a chemical composition comprising the molar relationship:

$$(x)X_2O_3:TO_2$$

wherein $0.01 \leq x \leq 0.2$; X is a trivalent element (e.g., one or more of B, Al, Ga, and Fe, especially Al); and T is a tetravalent element (e.g., one or more of Si, Ge, Sn, and Ti, especially Si).

In one aspect there is provided a molecular sieve having, in its as-synthesized form, an X-ray diffraction pattern including at least the peaks set forth in Table 3 below.

The molecular sieve has, in its as-synthesized and anhydrous form, a chemical composition comprising the molar relationship:

$$(m)M:(q)Q:(x)X_2O_3:TO_2$$

wherein $0<m\leq0.1$; $0<q\leq0.1$; $0.01\leq x\leq 0.2$; M is a Group 1 or 2 metal; Q comprises N-cyclohexylmethyl-N-ethylpyrrolidinium cations; X is a trivalent element (e.g., one or more of B, Al, Ga, and Fe, especially Al); and T is a tetravalent element (e.g., one or more of Si, Ge, Sn, and Ti, especially Si).

In one aspect, there is provided a method for preparing the molecular sieve described which comprises (a) preparing a reaction mixture containing (1) a source of an oxide of a tetravalent element; (2) a source of an oxide of a trivalent element; (3) a source of Group 1 or 2 metal; (4) hydroxide ions; (5) a structure directing agent comprising N-cyclohexylmethyl-N-ethylpyrrolidinium cations; and (6) water; and (b) subjecting the reaction mixture to crystallization conditions sufficient to form crystals of the molecular sieve.

In one aspect, there is provided a process for converting a feedstock comprising an organic compound to a conversion product which comprises the step of contacting the feedstock with a catalyst at organic compound conversion conditions, the catalyst comprising an active form of the molecular sieve described herein.

In one aspect, there is provided a process for catalytic reduction of nitrogen oxides ($NO_x$) in a gas stream, the process comprising contacting the gas stream containing $NO_x$ with a catalyst comprising the molecular sieve disclosed herein.

DETAILED DESCRIPTION

Introduction

Figure 1A:
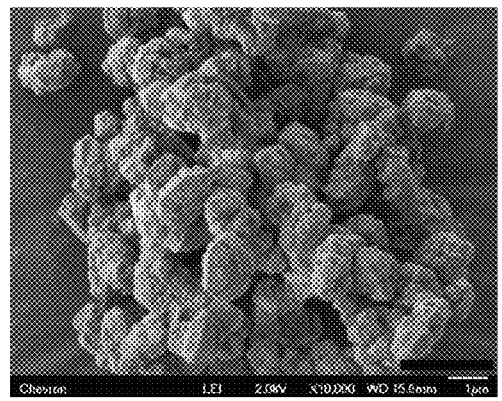
FIGS. 1(a), 1(b) and 1(c) are Scanning Electron Micrograph (SEM) images of the as-synthesized molecular sieve of Example 1 at different magnifications.

Described herein is a novel crystalline molecular sieve, which is designated SSZ-104, its synthesis in the presence of a structure directing agent comprising N-cyclohexylmethyl-N-ethylpyrrolidinium cations, and its use as an adsorbent and a catalyst.

Reaction Mixture

In general, molecular sieve SSZ-104 is prepared by: (a) preparing a reaction mixture containing (1) a source of an oxide of a tetravalent element (T); (2) a source of an oxide of a trivalent element (X); (3) a source of a Group 1 or 2 metal (M); (4) hydroxide ions; (5) a structure directing agent (Q) comprising N-cyclohexylmethyl-N-ethylpyrrolidinium cations; and (6) water; and (b) subjecting the reaction mixture to crystallization conditions sufficient to form crystals of the molecular sieve.

The composition of the reaction mixture from which the molecular sieve is formed, in terms of mole ratios, is identified in Table 1 below:

TABLE 1

|  | Broad | Exemplary |
|---|---|---|
| $TO_2/X_2O_3$ | ≥10 | 15 to 100 |
| $M/TO_2$ | 0.05 to 1.00 | 0.20 to 0.80 |
| $Q/TO_2$ | 0.05 to 0.50 | 0.05 to 0.30 |
| $OH/TO_2$ | 0.10 to 1.00 | 0.20 to 0.80 |
| $H_2O/TO_2$ | 15 to 60 | 15 to 40 | wherein T, X, M, and Q are defined as described herein above.

The tetravalent element T may be one or more of silicon (Si), germanium (Ge), tin (Sn), and titanium (Ti). Suitable sources of the tetravalent element T depend on the element T selected. Where the tetravalent element T is Si, sources useful for silicon oxide include fumed silica, colloidal silica, precipitated silica, alkali metal silicates, and tetraalkyl orthosilicates.

The trivalent element X may be one or more of boron (B), aluminum (Al), gallium (Ga), and iron (Fe). Suitable sources of the trivalent element X depend on the element X selected. Where the trivalent element X is Al, sources useful for aluminum oxide include hydrated alumina and water-soluble aluminum salts (e.g., aluminum nitrate).

Suitable sources of Group 1 or 2 metal (M) include metal oxide, metal hydroxide, metal chloride, metal fluoride, metal sulfate, metal nitrate, metal aluminate, and combinations thereof.

The structure directing agent (Q) comprises N-cyclohexylmethyl-N-ethylpyrrolidinium cations which has the following structure (1):

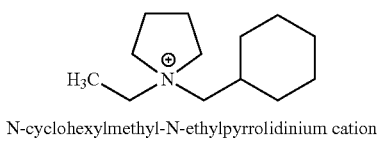

N-cyclohexylmethyl-N-ethylpyrrolidinium cation

Suitable sources of Q are the hydroxides and/or salts of the relevant quaternary ammonium compounds.

The reaction mixture may also contain seeds of a molecular sieve material, such as SSZ-104, from a previous synthesis, desirably in an amount of from 0.01 to 10,000 ppm by weight (e.g., from 100 to 5000 ppm by weight) of the reaction mixture.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization and Post-Synthesis Treatment

Crystallization of the molecular sieve can be carried out under either static, tumbled or stirred conditions in a suitable reactor vessel, such as for example polypropylene jars or Teflon-lined or stainless steel autoclaves, at a temperature of from 125° C. to 200° C. for a time sufficient for crystallization to occur at the temperature used (e.g., from 1 day to 21 days). The reaction mixture is usually reacted under autogenous pressure, or optionally in the presence of a gas such as nitrogen.

Once the molecular sieve crystals have formed, the solid product is separated from the reaction mixture by standard mechanical separation techniques such as centrifugation or filtration. The crystals are water-washed and then dried to obtain the as-synthesized molecular sieve crystals. The drying step is typically performed at a temperature of less than 200° C.

As a result of the crystallization process, the recovered crystalline molecular sieve product contains within its pore structure at least a portion of the structure directing agent used in the synthesis.

The structure directing agent is typically at least partially removed from the molecular sieve by calcination before use. Calcination consists essentially of heating the molecular sieve comprising the structure directing agent at a temperature of from 200° C. to 800° C. in the presence of an oxygen-containing gas, optionally in the presence of steam. The structure directing agent can also be removed by photolysis techniques as described in U.S. Pat. No. 6,960,327.

To the extent desired and depending on the $TO_2/X_2O_3$ molar ratio of the molecular sieve, any cations in the as-synthesized molecular sieve can be replaced in accordance with techniques well known in the art by ion exchange with other cations. Suitable replacing cations include metal ions, hydrogen ions, hydrogen precursor, e.g., ammonium ions and combinations thereof. Exemplary replacing cations are those which tailor the catalytic activity for certain organic conversion reactions or for the conversion of at least one compound comprising at least one nitrogen-oxygen bond. These include hydrogen, rare earth metals and metals of Groups 2 to 15 of the Periodic Table of the Elements.

Characterization of the Molecular Sieve

The novel molecular sieve structure SSZ-104 is characterized by an X-ray diffraction (XRD) pattern which, in the calcined form of the molecular sieve, includes at least the peaks set forth in Table 2 below and which, in the as-synthesized form of the molecular sieve, includes at least the peaks set forth in Table 3 below.

TABLE 2

Characteristic Peaks for Calcined SSZ-104

| 2-Theta[a] | d-Spacing, nm | Relative Intensity[b] |
|---|---|---|
| 7.51 | 1.176 | S |
| 9.63 | 0.918 | W |
| 12.51 | 0.707 | W |
| 12.96 | 0.682 | S |
| 15.11 | 0.586 | W |
| 16.26 | 0.545 | W |
| 17.87 | 0.496 | VS |
| 19.90 | 0.459 | S |
| 20.79 | 0.427 | VS |
| 21.73 | 0.409 | S |
| 22.18 | 0.401 | W |
| 22.57 | 0.394 | W |
| 26.09 | 0.341 | S |
| 28.17 | 0.317 | M |
| 30.27 | 0.295 | M |
| 30.87 | 0.289 | S |
| 31.75 | 0.282 | W |
| 33.57 | 0.267 | W |
| 34.72 | 0.258 | W |

[a] ±0.20
[b] The powder XRD patterns provided are based on a relative intensity scale in which the strongest line in the powder X-ray pattern is assigned a value of 100: W = weak (>0 to ≤20); M = medium (>20 to ≤40); S = strong (>40 to ≤60); and VS = very strong (>60 to ≤100).

TABLE 3

Characteristic Peaks for As-Synthesized SSZ-104

| 2-Theta[a] | d-Spacing, nm | Relative Intensity[b] |
|---|---|---|
| 7.51 | 1.177 | S |
| 9.70 | 0.911 | W |
| 12.48 | 0.709 | W |
| 12.97 | 0.682 | S |
| 15.14 | 0.585 | W |
| 16.22 | 0.546 | W |
| 17.74 | 0.500 | VS |
| 19.88 | 0.446 | S |
| 20.80 | 0.427 | VS |
| 21.66 | 0.410 | S |
| 22.01 | 0.404 | W |
| 22.54 | 0.394 | W |
| 26.08 | 0.341 | S |
| 28.18 | 0.316 | M |
| 30.21 | 0.296 | M |
| 30.92 | 0.289 | S |
| 33.42 | 0.268 | W |
| 34.72 | 0.258 | W |

[a] ±0.20
[b] The powder XRD patterns provided are based on a relative intensity scale in which the strongest line in the powder X-ray pattern is assigned a value of 100: W = weak (>0 to ≤20); M = medium (>20 to ≤40); S = strong (>40 to ≤60); and VS = very strong (>60 to ≤100).

The powder X-ray diffraction patterns presented herein were collected by standard techniques. The radiation was CuK$_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

In its calcined form, molecular sieve SSZ-104 has a chemical composition, comprising the molar relationship:

$$(x)X_2O_3:TO_2$$

wherein 0.01≤x≤0.2 (e.g., 0.02≤x≤0.2, 0.03≤x≤0.2, 0.04≤x≤0.2, 0.05≤x≤0.2, 0.06≤x≤0.2, 0.07≤x≤0.2, 0.08≤x≤0.2, 0.09≤x≤0.2, or 0.1≤x≤0.2); X is a trivalent element (e.g., one or more of B, Al, Ga, and Fe, especially Al); and T is a tetravalent element (e.g., one or more of Si, Ge, Sn, and Ti, especially Si).

In its as-synthesized and anhydrous form, molecular sieve SSZ-104 has a chemical composition comprising the molar relationship:

$$(m)M:(q)Q:(x)X_2O_3:TO_2$$

wherein 0<m≤0.1; 0<q≤0.1; 0.01≤x≤0.2 (e.g., 0.02≤x≤0.2, 0.03≤x≤0.2, 0.04≤x≤0.2, 0.05≤x≤0.2, 0.06≤x≤0.2, 0.07≤x≤0.2, 0.08≤x≤0.2, 0.09≤x≤0.2, or 0.1≤x≤0.2); M is a Group 1 or 2 metal; Q comprises N-cyclohexylmethyl-N-ethylpyrrolidinium cations; X is a trivalent element (e.g., one or more of B, Al, Ga, and Fe, particularly Al); and T is a tetravalent element (e.g., one or more of Si, Ge, Sn, and Ti, particularly Si). As used herein, the term "as-synthesized" refers to the molecular sieve in its form after crystallization, prior to removal of the structure directing agent. The term "anhydrous form" as used in the context of the present disclosure refers to a molecular sieve substantially devoid of both physically adsorbed and chemically adsorbed water.

Processes Using SSZ-104

Molecular sieve SSZ-104 can be used as an adsorbent or as a catalyst to catalyze a wide variety of chemical conversion processes including many of present commercial/industrial importance.

Before use in catalysis, molecular sieve SSZ-104 will normally be formulated into catalyst compositions by combination with other materials, such as binders and/or matrix materials, which provide additional hardness or catalytic activity to the finished catalyst.

Materials which can be blended with the molecular sieve can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of molecular sieve SSZ-104 contained in the final catalyst product ranges from 1 to 90 wt. % of the total catalyst composition (e.g., from 2 to 80 wt. % of the total catalyst composition).

Organic Conversion Processes

Molecular SSZ-104 may be useful as a catalyst in organic compound conversion processes. Examples of organic conversion processes which are effectively catalyzed by SSZ-104, by itself or in combination with one or more other catalytically active substances including other crystalline catalysts, include those requiring a catalyst with acid activity.

Molecular sieve SSZ-104 may be suitable for use as a catalyst in the conversion of oxygenates to olefins. As used herein, the term "oxygenates" is defined to include, but is not necessarily limited to aliphatic alcohols, ethers, carbonyl compounds (e.g., aldehydes, ketones, carboxylic acids, carbonates, and the like), and also compounds containing hetero-atoms, such as, halides, mercaptans, sulfides, amines, and mixtures thereof. The aliphatic moiety will normally contain from 1 to 10 carbon atoms (e.g., from 1 to 4 carbon atoms). Particularly suitable oxygenate compounds are methanol, dimethyl ether, or mixtures thereof, especially methanol.

Conversion of oxygenates may be carried out with the oxygenate (e.g., methanol) in the liquid or the vapor phase, in batch or continuous mode. When carried out in continuous mode, a weight hourly space velocity (WHSV), based on oxygenate, of 1 to 1000 h$^{-1}$ (e.g., 1 to 100 h$^{-1}$) may be used. An elevated temperature is generally required to obtain economic conversion rates (e.g., a temperature between 300° C. and 600° C. or between 400° C. and 500° C.). The catalyst may be in a fixed bed, or a dynamic, e.g., fluidized or moving, bed.

The oxygenate feedstock may be mixed with a diluent, inert under the reaction conditions (e.g., argon, nitrogen, carbon dioxide, hydrogen, or steam). The concentration of oxygenate in the feedstream may vary widely (e.g., from 5 to 90 mole percent of the feedstock). The pressure may vary within a wide range (e.g., from atmospheric to 500 kPa).

The olefin(s) produced typically have from 2 to 30 carbon atoms (e.g., from 2 to 8 carbon atoms, from 2 to 6 carbon atoms, or from 2 to 4 carbons atoms, and most preferably are ethylene and/or propylene).

Reduction of Nitrogen Oxides

Molecular sieve SSZ-104 may be used in a catalytic process involving the conversion of at least one compound comprising at least one nitrogen-oxygen bond. Particularly preferred are processes wherein molecular sieve SSZ-104 is used as a catalyst and/or catalyst support in a selective catalytic reduction (SCR) process. Selective catalytic reduction refers to the catalytic process of reducing nitrogen oxides (NO$_x$) in a gas stream to dinitrogen (N$_2$) using a nitrogenous reductant.

The term "nitrogen oxides" (NO$_x$), as used in the context of the present disclosure, designates the oxides of nitrogen, especially nitrogen monoxide (NO), nitrogen dioxide (NO$_2$), nitrogen peroxide (NO$_3$), dinitrogen oxide (N$_2$O), dinitrogen trioxide (N$_2$O$_3$), dinitrogen tetroxide (N$_2$O$_4$), and dinitrogen pentoxide (N$_2$O$_5$).

The nitrogen oxides which are reduced using a catalyst containing molecular sieve SSZ-104 may be obtained by any process (e.g., as a waste gas stream). Combustion of any fossil fuel generates some level of NO$_x$ due to high temperatures and the availability of oxygen and nitrogen from both the air and fuel. In one embodiment, the gas stream containing NO$_x$ is an exhaust gas from an internal combustion engine.

Therefore, the present disclosure also relates to a process for selectively reducing nitrogen oxides by contacting a gas stream containing $NO_x$ with a catalyst containing molecular sieve SSZ-104 under suitable reducing conditions. The contacting of the gas stream with the catalyst comprising molecular sieve SSZ-104 takes place at an elevated temperature compared to ambient temperature such as a temperature in the range of anywhere from 150° C. to 700° C. The gas stream preferably also contains one or more reducing agents (e.g., urea and/or ammonia) which are active in the SCR process when simultaneously contacted with both the catalyst and $NO_x$ contained in the gas stream.

For the selective reduction of nitrogen oxides, molecular sieve SSZ-104 may be used in the form of a molded catalyst, preferably as a molded catalyst wherein molecular sieve SSZ-104 is deposited on a suitable refractory carrier, such as on a "honeycomb" carrier.

The molecular sieve may contain a transition metal within or on it which is capable of catalyzing the reduction of the nitrogen oxides. The transition metal may be selected from one or more of chromium (Cr), manganese (Mn), rhenium (Re), molybdenum (Mo), iron (Fe), ruthenium (Ru), cobalt (Co), rhodium (Rh), iridium (Ir), nickel (Ni), palladium (Pd), platinum (Pt), copper (Cu), silver (Ag), and zinc (Zn).

Any suitable and effective amount of at least one transition metal may be used in the catalyst. The total amount of the transition metal that may be included in the molecular sieve may be from 0.1 to 10 wt. % (e.g., 0.5 to 5 wt. %), based on the total weight of the molecular sieve.

The reduction of nitrogen oxides may be carried out in the presence of oxygen or in the absence of oxygen.

EXAMPLES

The following illustrative examples are intended to be non-limiting.

Example 1

Synthesis of SSZ-104

In a 23 mL Teflon liner, 1.07 mmol of N-cyclohexylmethyl-N-ethylpyrrolidinium hydroxide, 0.83 g of 1N NaOH solution, 1.56 g of sodium silicate solution, and 0.27 g of zeolite Y(CBV300, Zeolyst International, $SiO_2/Al_2O_3$ mole ratio=5.1) were all mixed and thoroughly stirred until a homogenous mixture was obtained. The liner was capped and placed within a Parr steel autoclave reactor. The autoclave was then fixed in a rotating spit (43 rpm) within an oven heated at 135° C. for 7-10 days. The solid products were recovered, washed thoroughly with deionized water and dried.

The resulting product was analyzed by powder XRD and indicated that the material is unique.

Figure 1B:
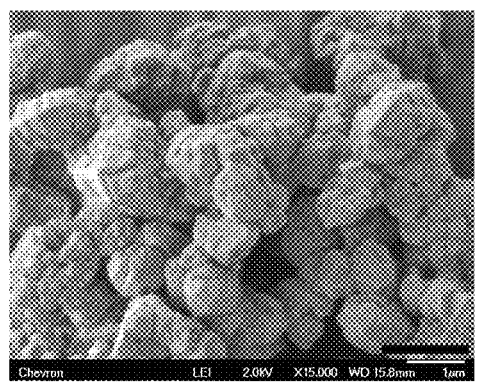
Figure 1C:
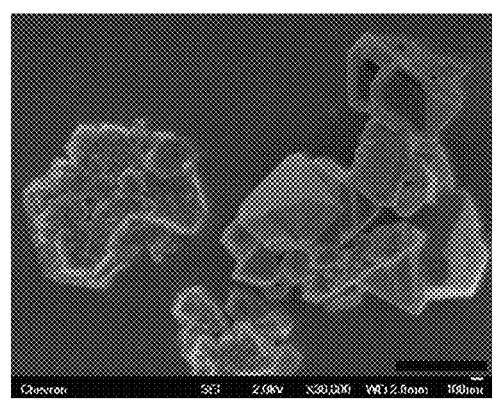

FIGS. 1(a), 1(b) and 1(c) are SEM images of the resulting product at different magnifications.

The product had a $SiO_2/Al_2O_3$ mole ratio of 7.6, as determined by ICP elemental analysis.

Example 2

Calcination of SSZ-104

The as-synthesized product of Example 1 was calcined inside a muffle furnace under a flow of air heated to 595° C. at a rate of 1° C./minute and held at 595° C. for 5 hours, cooled and then analyzed by powder XRD. The powder XRD pattern of the calcined molecular sieve is shown in FIG. 3 and indicates that the material remains stable after calcination to remove the organic SDA.

Example 3

Micropore Volume Analysis

The calcined product of Example 2 was subjected to a micropore volume analysis using $N_2$ as adsorbate and via the BET method. The zeolite in its sodium form exhibited a micropore volume of 0.18 $cm^3/g$ and indicates that SSZ-104 has microporous character. After ion exchange, the proton form of the zeolite had a micropore volume of 0.22 $cm^3/g$.

Example 4

$NO_x$ Performance of Copper-Loaded SSZ-104

A sample of an $NH_4^+$ form of SSZ-104 was added to a copper acetate solution at room temperature to produce a copper-exchanged molecular sieve. The copper-exchanged molecular was dried and calcined at 500° C. and resulted in a molecular sieve having about 3 wt. % copper based on the weight of the molecular sieve.

Copper-loaded SSZ-104 was then applied as a washcoat to a monolith honeycomb core and tested using a Synthetic Catalyst Activity Test (SCAT) rig. The testing was performed under simulated diesel exhaust gas conditions, namely exposing the catalyst to a gas at a space velocity of 50,000/hour, wherein the gas composition was about 350 ppm $NH_3$ and NO, about 14 weight % $O_2$, about 4.5 weight % $H_2O$, and about 5 weight % $CO_2$ in $N_2$. The test temperature ranged from 150 to 500° C.

Figure 2:
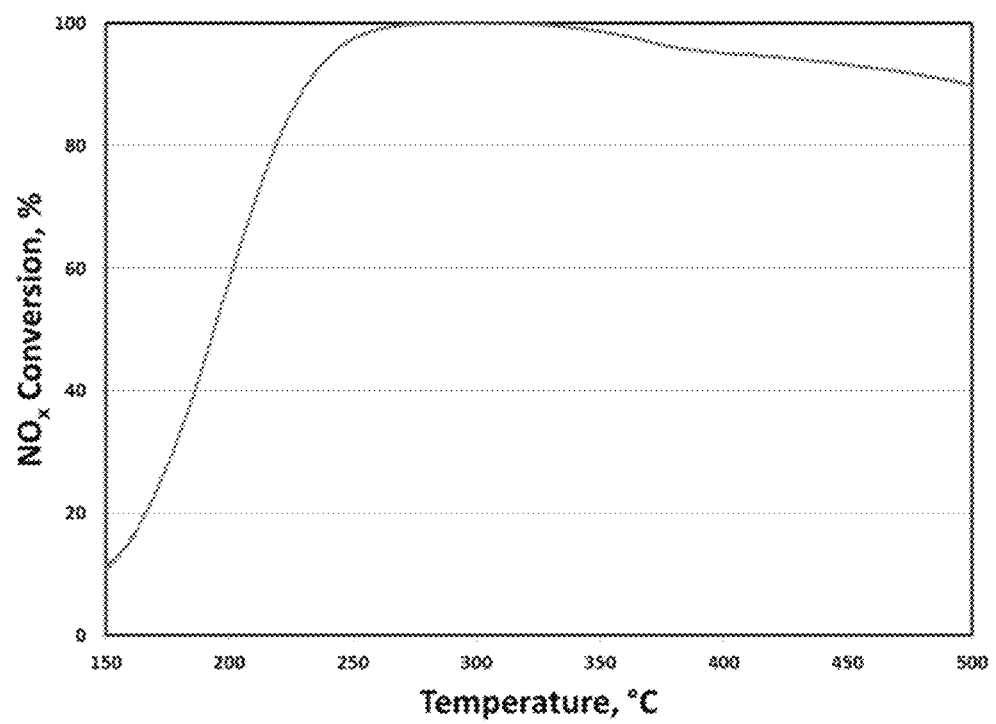
FIG. 2 is a graph illustrating $NO_x$ conversion based on temperature of copper-exchanged pure molecular sieve support SSZ-104 following calcination.

The sample was tested to determine its capacity for $NO_x$ conversion (e.g. into $N_2$ and $O_2$) as a function of temperature. The results are shown in FIG. 2.

As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

All documents cited in this application are herein incorporated by reference in their entirety to the extent such disclosure is not inconsistent with this text.

The invention claimed is:

1. A crystalline molecular sieve having, in its calcined form, an X-ray diffraction pattern including the peaks listed in the following table:

| 2-Theta | d-Spacing, nm | Relative Intensity |
|---|---|---|
| 7.51 ± 0.20 | 1.176 | S |
| 9.63 ± 0.20 | 0.918 | W |
| 12.51 ± 0.20 | 0.707 | W |
| 12.96 ± 0.20 | 0.682 | S |
| 15.11 ± 0.20 | 0.586 | W |
| 16.26 ± 0.20 | 0.545 | W |
| 17.87 ± 0.20 | 0.496 | VS |
| 19.90 ± 0.20 | 0.459 | S |
| 20.79 ± 0.20 | 0.427 | VS |
| 21.73 ± 0.20 | 0.409 | S |
| 22.18 ± 0.20 | 0.401 | W |
| 22.57 ± 0.20 | 0.394 | W |

| 2-Theta | d-Spacing, nm | Relative Intensity |
|---|---|---|
| 26.09 ± 0.20 | 0.341 | S |
| 28.17 ± 0.20 | 0.317 | M |
| 30.27 ± 0.20 | 0.295 | M |
| 30.87 ± 0.20 | 0.289 | S |
| 31.75 ± 0.20 | 0.282 | W |
| 33.57 ± 0.20 | 0.267 | W |
| 34.72 ± 0.20 | 0.258 | W. |

2. The molecular sieve of claim 1, having a chemical composition comprising the molar relationship:

$$(x)X_2O_3:TO_2$$

wherein $0.01 \leq x \leq 0.2$; X is a trivalent element; and T is a tetravalent element.

3. The molecular sieve of claim 2, wherein trivalent element X includes one or more of B, Al, Ga, and Fe; and tetravalent element T includes one or more of Si, Ge, Sn, and Ti.

4. The molecular sieve in claim 2, wherein trivalent element X includes Al and tetravalent element T includes Si.

5. A process for converting a feedstock comprising an organic compound to a conversion product, the process comprising contacting the feedstock with a catalyst at organic compound conversion conditions, the catalyst comprising an active form of the molecular sieve of claim 1.

6. A process for selectively reducing nitrogen oxides ($NO_x$), the process comprising contacting a gas stream containing $NO_x$ with a catalyst comprising the molecular sieve of claim 1.

7. The process of claim 6, wherein the molecular sieve contains a transition metal selected from one or more of Cr, Mo, Mn, Re, Fe, Ru, Co, Rh, Ir, Ni, Pd, Pt, Cu, and Zn.

8. The process of claim 6, wherein the gas stream is an exhaust gas stream of an internal combustion engine.

9. A crystalline molecular sieve having, in its as-synthesized form, an X-ray diffraction pattern including the peaks listed in the following table:

| 2-Theta | d-Spacing, nm | Relative Intensity |
|---|---|---|
| 7.51 ± 0.20 | 1.177 | S |
| 9.70 ± 0.20 | 0.911 | W |
| 12.48 ± 0.20 | 0.709 | W |
| 12.97 ± 0.20 | 0.682 | S |
| 15.14 ± 0.20 | 0.585 | W |
| 16.22 ± 0.20 | 0.546 | W |
| 17.74 ± 0.20 | 0.500 | VS |
| 19.88 ± 0.20 | 0.446 | S |
| 20.80 ± 0.20 | 0.427 | VS |
| 21.66 ± 0.20 | 0.410 | S |
| 22.01 ± 0.20 | 0.404 | W |
| 22.54 ± 0.20 | 0.394 | W |
| 26.08 ± 0.20 | 0.341 | S |
| 28.18 ± 0.20 | 0.316 | M |
| 30.21 ± 0.20 | 0.296 | M |
| 30.92 ± 0.20 | 0.289 | S |
| 33.42 ± 0.20 | 0.268 | W |
| 34.72 ± 0.20 | 0.258 | W. |

10. The molecular sieve of claim 9, having a chemical composition comprising the molar relationship:

$$(m)M:(q)Q:(x)X_2O_3:TO_2$$

wherein:
(a) $0 < m \leq 0.1$;
(b) $0 < q \leq 0.1$;
(c) $0.01 \leq x \leq 0.2$;
(d) M is a Group 1 or 2 metal;
(e) Q comprises N-cyclohexylmethyl-N-ethylpyrrolidinium cations;
(f) X is a trivalent element; and
(g) T is a tetravalent element.

11. The molecular sieve of claim 10, wherein trivalent element X includes one or more of B, Al, Ga, and Fe; and tetravalent element T includes one or more of Si, Ge, Sn, and Ti.

12. The molecular sieve of claim 10, wherein trivalent element X includes Al and tetravalent element T includes Si.

13. A method of preparing the molecular sieve of claim 9, comprising:
(a) preparing a reaction mixture containing:
(1) a source of an oxide of a tetravalent element (T);
(2) a source of an oxide of a trivalent element (X);
(3) a source of a Group 1 or 2 metal (M);
(4) hydroxide ions;
(5) a structure directing agent (Q) comprising N-cyclohexylmethyl-N-ethylpyrrolidinium cations; and
(6) water; and
(b) subjecting the reaction mixture to crystallization conditions sufficient to form crystals of the molecular sieve.

14. The method of claim 13, wherein the reaction mixture comprises, in terms of mole ratios, the following:

| | |
|---|---|
| $TO_2/X_2O_3$ | ±10 |
| $M/TO_2$ | 0.05 to 1.00 |
| $Q/TO_2$ | 0.05 to 0.50 |
| $OH/TO_2$ | 0.10 to 1.00 |
| $H_2O/TO_2$ | 15 to 60. |

15. The method of claim 13, wherein the reaction mixture comprises, in terms of mole ratios, the following:

| | |
|---|---|
| $TO_2/X_2O_3$ | 15 to 100 |
| $M/TO_2$ | 0.20 to 0.80 |
| $Q/TO_2$ | 0.05 to 0.30 |
| $OH/TO_2$ | 0.20 to 0.80 |
| $H_2O/TO_2$ | 15 to 40. |

* * * * *